Figure 1:
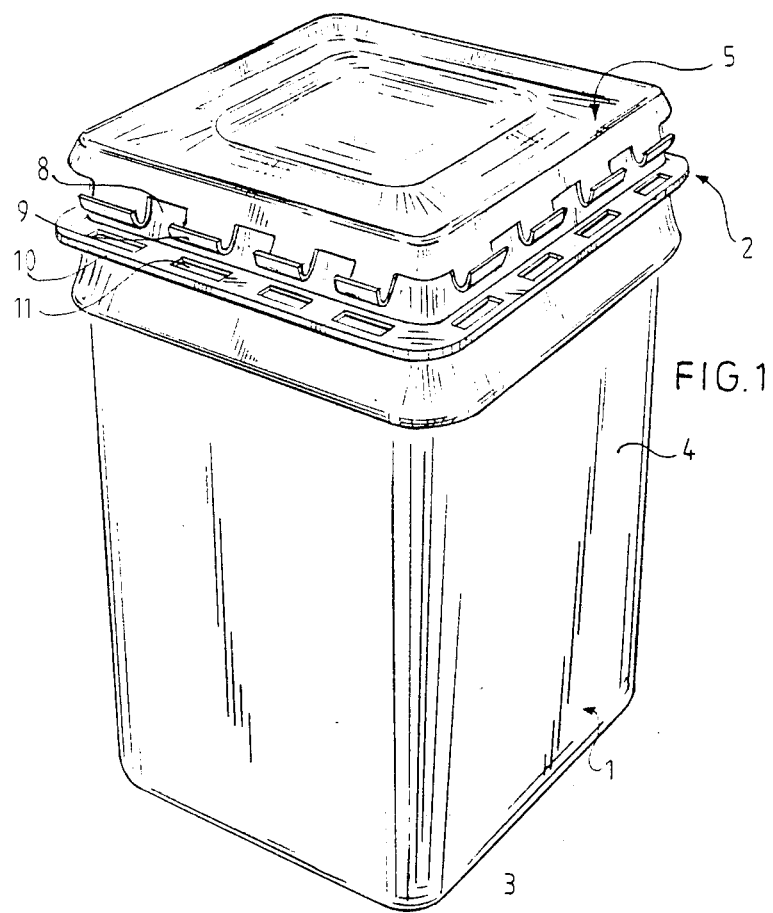

United States Patent [19]

Jonkers

[11] Patent Number: 4,585,138

[45] Date of Patent: Apr. 29, 1986

[54] CONTAINER WITH LOCKING COVER

[75] Inventor: Godefridus H. J. Jonkers, Helmond, Netherlands

[73] Assignee: Wiva Verpakkingen B.V., Netherlands

[21] Appl. No.: 750,520

[22] Filed: Jul. 1, 1985

[30] Foreign Application Priority Data

Jul. 2, 1984 [NL] Netherlands ............... 8402103

[51] Int. Cl.$^4$ ................ B65D 6/34; B65D 8/04; B65D 8/06
[52] U.S. Cl. ............................ 220/67; 220/306; 220/308
[58] Field of Search ............. 220/67, 306, 307, 308, 220/309

[56] References Cited

U.S. PATENT DOCUMENTS 3,297,193  1/1967  Stevens, Jr. et al. ............. 220/306
3,840,152  10/1974  Hodge ............................... 220/306
4,457,447  7/1984  Kirkis ............................... 220/308

Primary Examiner—George T. Hall
Attorney, Agent, or Firm—John P. Snyder

[57] ABSTRACT

A container, particularly suited to storing sensitive products such as contaminated waste, for example hospital refuse, the container 1 having a base with adjoining upright wall members 4, whereby the open top bounded by the upper edges of the wall members can be closed by a cover 5, whose rim is supported by the upper edges of the wall members, wherein the rim of the cover displays a groove or channel 6 which can accommodate the top edge of the upright wall members, whereby the rim of the cover and the upper edge of the container are provided with integral locking means 8,9,10 for permanently fixing the cover 5 to the container 1, and a sealing means 7, 12 is fitted in the channel, to close the container temporarily while permanent locking of the cover is easy to perform manually, and, moreover, can be confirmed visually.

28 Claims, 4 Drawing Figures

U.S. Patent   Apr. 29, 1986   4,585,138

CONTAINER WITH LOCKING COVER

The invention relates to a container, particularly suited to storing sensitive products such as contaminated waste, for example hospital refuse, the container having a base with adjoining upright wall members, whereby the open top bounded by the upper edges of the wall members can be closed by a cover, whose rim is supported by the upper edges of the wall members.

Such a container or cover is particularly intended for once-only usage. The container needs only to be filled and closed, after which it is brought to a waste-disposal plant, for example to be incinerated. Considering that such a container is not necessarily filled at once, but gradually, it is necessary that the cover can be removed regularly from the container, and then replaced airtight. When the container is full, the cover must be permanently fastened onto the container, a purpose for which external means of clamping such as clamping strips are often used, which are not only difficult to handle, but are also difficult to process during waste disposal.

The aim of the invention is to provide a container with a locking cover which is easy for the operating personnel to handle, that is to say, it is easy for them to close the container temporarily, while permanent locking of the cover is easy to perform manually, and, moreover, can be confirmed visually.

To that end, the invention provides a container which is distinguished in that the rim of the cover displays a groove or channel which can accommodate the top edge of the upright wall members, or vice versa, whereby the rim of the cover and the upper edge of the container are provided with integral locking means for permanently fixing the cover to the container, and a sealing means is fitted in the channel.

The proposed sealing means provides for both a temporary closure between container and cover, which allows the cover to be removed again, and a permanent closure, when the cover is locked onto the container. Thanks to the integral locking means, a permanent closure is assured, because no locking devices can be omitted, as can happen, for example, due to loss, when the usual separate locking means are used.

In the preferred embodiment, a sealing means is provided by a rib formed on an edge member, which serves to eliminate the clearance between the respective edge members in the groove. A rib of this kind provides a temporary closure before the cover is permanently locked onto the container.

An extra measure, a strip of deformable material situated in the bottom of the groove can serve as an extra means of sealing, the strip ensuring a permanent closure as soon as the cover is finally locked in place.

Preferably, the locking means is in each case formed by a first abutment surface formed on the cover, and a second abutment surface formed on the container wall member, whereby the distance between the first abutment surface and the bottom of the groove is less than the sum of the thickness of the deformable strip and the distance from the second abutment surface to the top edge of the wall member.

In a particularly simple embodiment, the first abutment surface of the locking means is in each case formed by a transverse surface of a flexible downward-projecting flange around the circumference of the cover.

If the cover is formed, for example, by means of injection moulding, it is advantageous, from the point of view of obtaining a releasing form, to situate the first abutment on the outer edge (with respect to the cover) of the flange, the flange being cut away in a number of places, whereby the projecting rib on the container wall members which bears the second abutment surface is provided with apertures for the insertion of the remaining portions of the flange.

A particularly smooth locking action can be obtained by giving the remaining portions of the flange a V-shape (in elevated section).

The invention will be further clarified by reference to the following description with figures of a number of embodiments.

IN THE DRAWINGS

FIG. 1 shows a perspective view of a container fitted with a cover, according to the invention, the cover not yet being locked on.

Figure 2:
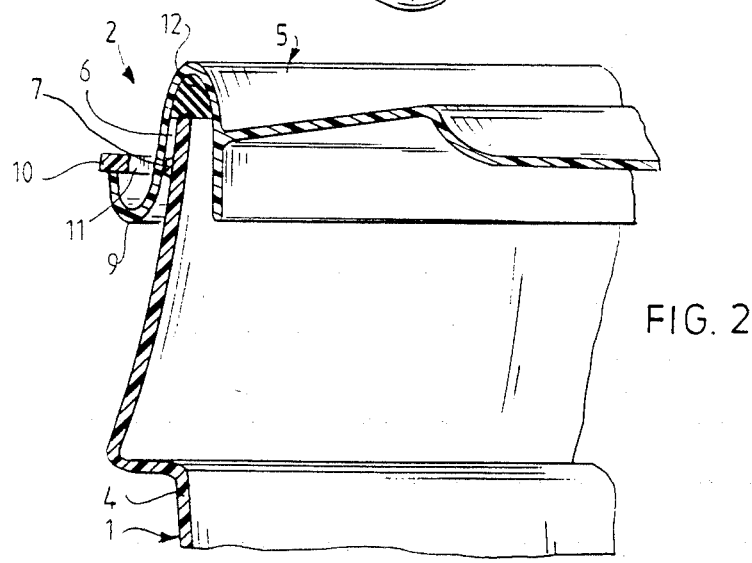
Figure 3:
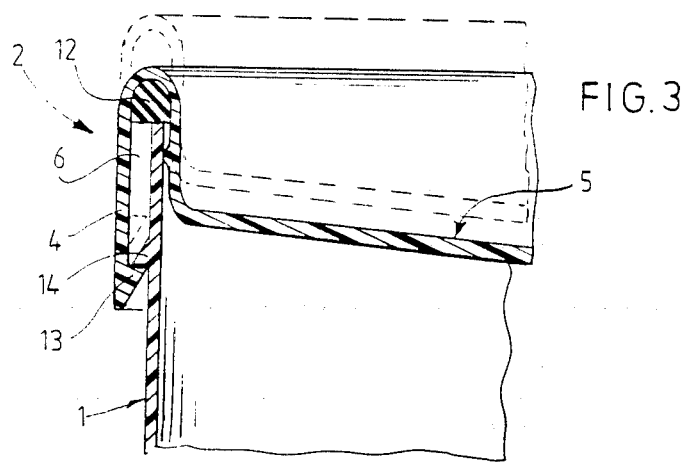
Figure 4:
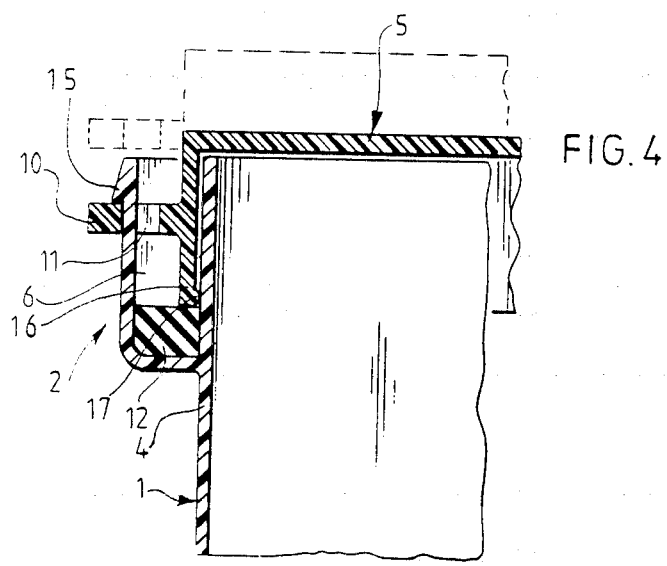

FIGS. 2, 3 and 4 each show an elevated section of the edge members of the container and cover, in a locked position.

In FIG. 1, reference number 1 indicates a container made of an arbitrary material, preferably plastic. The container can be made by arbitrary production processes, but by preference can be made by a blow moulding procedure, whereby the projection rib 2 can be integrally moulded at the same time.

The container has a base 3, upon which there are adjoined the air-tight and light-proof standing wall members 4 which terminate at the top with the above mentioned projecting rib 2, which borders the open top of the container. In the embodiment shown, four wall members 4 are indicated, but it will be clear that wall members 4 can have a circular or conical shape.

The open top can be closed off by a cover 5, which can also be made of an arbitrary material.

In FIGS. 2, 3 and 4 there is in each case shown a detail of the edge members of container 1 and cover 5.

According to a feature of the invention, either along the edge of cover 5, (see FIGS. 2 and 3) or in the edge member of container 1 (see FIG. 4) there is provided a channel 6. The breadth of the channel 6 is such that the cover 5 is easy to remove in an upwards direction. On the inner wall of groove 6 there is situated a rib 7, which closes airtight on the outside of the upper edge member of the standing walls 4.

The outer wall of groove 6 is formed as a flexible flange, which is cut away at a number of places, 8 (see FIG. 1), so that the flexible locking tabs 9 remain. In elevation these have a V-shape (see FIG. 2). The upper edge of the vertical wall members 4 is provided with an integral rib, 10, which is also cut away in a number of places, 11. These apertures 11 correspond with the V-shaped flexible tabs 9 of the cover flange, such that, together, they form the means of locking.

Finally, in the bottom of groove 6, a deformable sealing strip 12, is fitted.

The container can be used as follows. When cover 5 is placed normally on the top edge projection of standing wall members 4, groove 6 of the cover will fall over the upper edge of the wall members, whereby rib 7 forms a temporary seal. Cover 5 can be removed whenever required. As soon as the container is full, the cover can be pushed down in such a way that flexible tabs 9 pass through the apertures in rib 10, until the turned-up part of each tab 9 falls into place against the underside of rib 10. By this means, a permanent locking takes place, such that the container is definitely closed. A permanent seal is assured because of the sealing strip 12.

FIG. 3 shows an alternative embodiment, in which groove 6 or cover 5 has a rib 13, on the inner side of the outer wall, which rib closes against the outside of the upright wall members 4 of the container. The outer wall of the container displays an abutment rib, 14, behind which abutment rib 13 can be engaged, as soon as the cover is pushed down from the position shown by broken lines in FIG. 3, in the manner described above, to the position drawn with unbroken lines. On the one hand, a temporary seal is provided in this way by rib 13, and on the other hand a permanent seal is provided by sealing strip 12 in the bottom of groove 6 and the engagement between abutment ribs 13 and 14. The flexible downward-directed outer side of groove 6 is, in this embodiment, not cut away, and forms a continuous rim which is sufficiently stiff and robust to ensure a permanent locking.

FIG. 4 shown an embodiment in which the groove or channel 6 is situated in the upper edge of the standing wall members 4 of container 1. The outer wall of groove 6 is provided with incisions, corresponding to the incisions 8 in the cover shown in FIG. 1, so that tabs corresponding to those indicated by 9 in FIG. 1 are left over. Each tab can be pushed through an aperture, 11 in a rib 10, which is integral to the cover, in order to bring about locking between the cover and the container. For this purpose, the flexible remaining tab of channel 6 is made with an abutment rib 15, which engages behind the upper surface of rib 10.

The downward projecting edge 16, of cover 5 is provided with a rib 17, on the inner side, to obtain a temporary closure.

Finally, it should be pointed out that, of all the embodiments shown, that in FIG. 2 is the easiest to cast in an injection mould. Thanks to the S-shape of the edge member of cover 5, the form is fully releasing, such that particularly simple mould forms can be used, thus bringing down the cost.

Obviously, the invention is not restricted to the embodiments described above.

What is claimed is:

1. Container, particularly for the storage of sensitive products, for example contaminated waste such as hospital refuse, the container having a base and joining thereupon standing wall members, whereby the open top bordered by the upper edges of the wall members can be closed by a cover, whose edge member is carried by the upper edges of the standing wall members, characterized in that the edge member of the cover displays a groove or channel for accomodating the upper edge of the wall members (4), or vice-versa, whereby the edge member and upper edge are provided with integral means of locking (9-11) for permanently closing cover (5) and container (1) together, and that a means of sealing (7, 12, 13, 17) is fitted in channel (6).

2. Container as claimed in claim 1, characterized in that the sealing means is at least one flexible rib (7, 13, 17) for taking up the clearance between both edges.

3. Container as claimed in claim 1 characterized in that the means of sealing is a strip of deformable material fitted in the bottom of the groove.

4. Container as claimed in claim 1, characterized in that each locking means is formed by a first abutment surface formed on the cover (5) and a second abutment surface formed on the wall member (4) of the container, whereby the distance from the first abutment surface to the bottom of the groove is less than the sum of the thickness of the deformable strip (12) and the distance from the second abutment surface to the end edge of the wall member (4).

5. Container as claimed in claim 4, characterized in that the first abutment surface of each locking means is formed by a transverse surface of a flexible downward-directed tab on the circumference of the cover (5).

6. Container as claimed in claim 4 characterized in that the first abutment surface is situated, with respect to the cover, on the outer edge of the flange, the flange being cut away in a number of places, and in that in the projecting rib (10) which bears the second abutment surface, apertures (11) are made through which the remaining parts of the flange can be inserted.

7. Container as claimed in claim 6, characterized in that the flange 9, in elevated section, forms a V-shape.

8. Container as claimed in claim 2 characterized in that the means of sealing is a strip of deformable material fitted in the bottom of the groove.

9. Container as claimed in claim 2 characterized in that each locking means is formed by a first abutment surface formed on the cover and a second abutment surface formed on the wall member of the container, whereby the distance from the first abutment surface to the bottom of the groove is less than the sum of the thickness of the deformable strip and the distance from the second abutment surface to the end edge of the wall member.

10. Container as claimed in claim 3 characterized in that each locking means is formed by a first abutment surface formed on the cover and a second abutment surface formed on the wall member of the container, whereby the distance from the first abutment surface to the bottom of the groove is less than the sum of the thickness of the deformable strip and the distance from the second abutment surface to the end edge of the wall member.

11. Container as claimed in claim 8 characterized in that each locking means is formed by a first abutment surface formed on the cover and a second abutment surface formed on the wall member of the container, whereby the distance from the first abutment surface to the bottom of the groove is less than the sum of the thickness of the deformable strip and the distance from the second abutment surface to the end edge of the wall member.

12. Container as claimed in claim 9 characterized in that the first abutment surface of each locking means is formed by a transverse surface of a flexible downward-directed tab on the circumference of the cover.

13. Container as claimed in claim 10 characterized in that the first abutment surface of each locking means is formed by a transverse surface of a flexible downward-directed tab on the circumference of the cover.

14. Container as claimed in claim 11 characterized in that the first abutment surface of each locking means is formed by a transverse surface of a flexible downward-directed tab on the circumference of the cover.

15. Container as claimed in claim 9 characterized in that the first abutment surface is situated, with respect to the cover, on the outer edge of the flange, the flange being cut away in a number of places, and in that in the projecting rib which bears the second abutment surface, apertures are made through which the remaining parts of the flange can be inserted.

16. Container as claimed in claim 10 characterized in that the first abutment surface is situated, with respect to the cover, on the outer edge of the flange, the flange being cut away in a number of places, and in that in the projecting rib which bears the second abutment surface, apertures are made through which the remaining parts of the flange can be inserted.

17. Container as claimed in claim 11 characterized in that the first abutment surface is situated, with respect to the cover, on the outer edge of the flange, the flange being cut away in a number of places, and in that in the projecting rib which bears the second abutment surface, apertures are made through which the remaining parts of the flange can be inserted.

18. Container as claimed in claim 5 characterized in that the first abutment surface is situated, with respect to the cover, on the outer edge of the flange, the flange being cut away in a number of places, and in that in the projecting rib which bears the second abutment surface, apertures are made through which the remaining parts of the flange can be inserted.

19. Container as claimed in claim 12 characterized in that the first abutment surface is situated, with respect to the cover, on the outer edge of the flange, the flange being cut away in a number of places, and in that in the projecting rib which bears the second abutment surface, apertures are made through which the remaining parts of the flange can be inserted.

20. Container as claimed in claim 13 characterized in that the first abutment surface is situated, with respect to the cover, on the outer edge of the flange, the flange being cut away in a number of places, and in that in the projecting rib which bears the second abutment surface, apertures are made through which the remaining parts of the flange can be inserted.

21. Container as claimed in claim 14 characterized in that the first abutment surface is situated, with respect to the cover, on the outer edge of the flange, the flange being cut away in a number of places, and in that in the projecting rib which bears the second abutment surface, apertures are made through which the remaining parts of the flange can be inserted.

22. Container as claimed in claim 15 characterized in that the flange, in elevated section, forms a V-shape.

23. Container as claimed in claim 16 characterized in that the flange, in elevated section, forms a V-shape.

24. Container as claimed in claim 17 characterized in that the flange, in elevated section, forms a V-shape.

25. Container as claimed in claim 18 characterized in that the flange, in elevated section, forms a V-shape.

26. Container as claimed in claim 19 characterized in that the flange, in elevated section, forms a V-shape.

27. Container as claimed in claim 20 characterized in that the flange, in elevated section, forms a V-shape.

28. Container as claimed in claim 21 characterized in that the flange, in elevated section, forms a V-shape.

* * * * *

REEXAMINATION CERTIFICATE (3239th)

United States Patent [19]

Jonkers

[11] B1 4,585,138
[45] Certificate Issued Jun. 24, 1997

[54] CONTAINER WITH LOCKING COVER

[75] Inventor: Godefridus H. J. Jonkers, Helmond, Netherlands

[73] Assignee: Wiva Verpakkingen B.V., Oosterho, Netherlands

Reexamination Request:
No. 90/004,126, Jan. 30, 1996

Reexamination Certificate for:
Patent No.: 4,585,138
Issued: Apr. 29, 1986
Appl. No.: 750,520
Filed: Jul. 1, 1985

[51] Int. Cl.$^6$ .................. B65D 6/34; B65D 8/04; B65D 8/06; B65D 41/18
[52] U.S. Cl. .................. 220/615; 220/614; 220/784; 220/795; 220/786; 588/900
[58] Field of Search .................. 215/209, 216, 215/224; 220/306, 307, 308, 309, 310, 315, 324, 326, 281, 614, 795, 784, 786, 780, 615

[56] References Cited

U.S. PATENT DOCUMENTS

| | | |
|---|---|---|
| 3,297,193 | 1/1967 | Stevens, Jr. . |
| 3,464,582 | 9/1969 | Greitzer et al. .................. 220/306 |
| 3,503,643 | 3/1970 | Alfaro .................. 220/315 X |
| 3,840,152 | 10/1974 | Hodge . |
| 3,848,767 | 11/1974 | Naf .................. 220/308 |
| 3,940,008 | 2/1976 | Flanders .................. 220/326 X |
| 4,043,482 | 8/1977 | Brown .................. 220/795 X |
| 4,212,415 | 7/1980 | Neely .................. 220/324 X |
| 4,457,447 | 7/1984 | Kirkis . |
| 4,560,083 | 12/1985 | Danico .................. 220/786 |

FOREIGN PATENT DOCUMENTS 25 49 932  11/1975  Germany .

*Primary Examiner*—Allan N. Shoap

[57] ABSTRACT

A container, particularly suited to storing sensitive products such as contaminated waste, for example hospital refuse, the container 1 having a base with adjoining upright wall members 4, whereby the open top bounded by the upper edges of the wall members can be closed by a cover 5, whose rim is supported by the upper edges of the wall members, wherein the rim of the cover displays a groove or channel 6 which can accommodate the top edge of the upright wall members, whereby the rim of the cover and the upper edge of the container are provided with integral locking means 8,9,10 for permanently fixing the cover 5 to the container 1, and a sealing means 7, 12 is fitted in the channel, to close the container temporarily while permanent locking of the cover is easy to perform manually, and, moreover, can be confirmed visually.

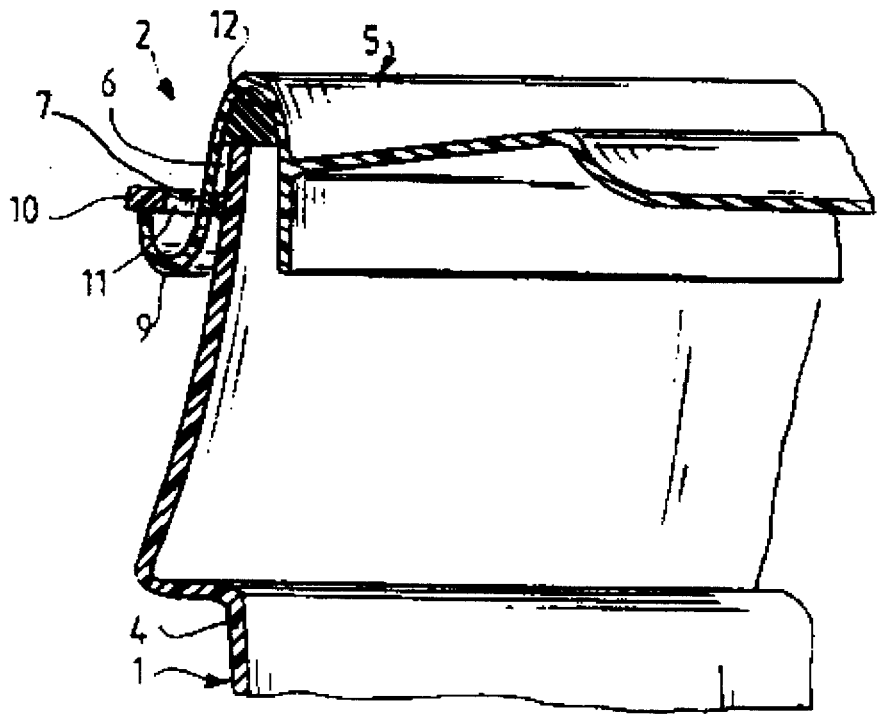

//B1 4,585,138

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–28 are cancelled.

New claims 29–39 are added and determined to be patentable.

29. *A container for the storage of hospital refuse which is to be incinerated absent opening of the container, the container having a base and joining thereupon standing wall members, an open top bordered by the upper edges of the wall members defining a peripherally continuous uppermost seal-forming edge being adapted to be closed by a cover (5), said cover having an edge member seated upon the upper edges of the standing wall members, the cover edge member includes a peripherally continuous wall portion defining an axially downwardly opening groove receiving the upper edges of the wall members (4), the cover edge member and the upper edges are provided with respective integral locking means (9–11) for permanently locking the cover (5) and container (1) together, means for sealing (7, 12, 13, 17) against said peripherally continuous uppermost seal-forming edge is housed in said groove (6), one of said integral locking means being formed by a plurality of peripherally spaced flexible tabs (9) projecting radially outwardly, each flexible tab (9) being provided with a first abutment surface, another of said integral locking means being formed by a peripherally continuous radially outwardly protruding rib (10) provided with a plurality of peripherally spaced apertures (11), each aperture receiving one of said flexible tabs (9) and a second abutment surface defined by said protruding rib against which abut the first abutment surfaces when the cover (5) is locked to the container (1), said peripherally continuous radially outwardly protruding rib (10) being disposed axially below said peripherally continuous uppermost seal-forming edge, said apertures (11) being radially outwardly spaced from said wall members and said upper edges, said sealing means (7, 12, 13, 17) being a separate strip (12) of deformable material fitted in a bottom of the groove (6), and the distance from the first abutment surface to the bottom of the groove (6) is less than the sum of the thickness of the deformable strip (12) and the distance from the second abutment surface to the uppermost seal-forming edge whereby upon the locking of the cover (5) to the container (1) the separate strip (12) will be compressed by and sealed against said peripherally continuous uppermost seal-forming edge.*

30. *The container as defined in claim 29 wherein said protruding rib (10) is carried by said wall members (4) of said container (1).*

31. *The container as defined in claim 29 wherein said protruding rib (10) protrudes substantially radially outwardly of said wall members (4) of said container (1).*

32. *The container as defined in claim 29 wherein said protruding rib (10) protrudes substantially radially outwardly of said wall members (4) of said container (1), and said apertures (11) open substantially axially through said protruding rib (10).*

33. *The container as defined in claim 29 wherein said flexible tabs (9) and protruding rib (10) include respective tab terminal end portion and a protruding rib terminal end portion, and said first and second abutment surfaces are located substantially at said respective tab terminal end portion and said protruding rib terminal end.*

34. *The container as defined in claim 29 wherein said flexible tabs (9) and protruding rib (10) include respective tab terminal end portion and a protruding rib terminal end portion, said first and second abutment surfaces are located substantially at said respective tab terminal end portion and said protruding rib terminal end, and each tab terminal end portion projects at least partially into an associated aperture (11).*

35. *The container as defined in claim 29 wherein said flexible tabs (9) and protruding rib (10) includes respective tab terminal end portion and a protruding rib terminal end portion, said first and second abutment surfaces are located substantially at said respective tab terminal end portion and said protruding rib terminal end, each tab terminal end portion projects through an associated aperture, and each tab terminal end portion has a free edge defining said first abutment surface.*

36. *The container as defined in claim 29 wherein said flexible tabs (9) and protruding rib (10) include respective tab terminal end portion and a protruding rib terminal end portion, said first and second abutment surfaces are located substantially at said respective tab terminal end portion and said protruding rib terminal end, each tab terminal end portion projects through an associated aperture, each tab terminal end portion has a free edge defining said first abutment surface, each tab terminal end portion projects generally axially upwardly toward said cover (5), and said second abutment surface is a lower surface of said protruding rib (10).*

37. *The container as defined in claim 30 wherein said flexible tabs (9) and protruding rib (10) include respective tab terminal end portion and a protruding rib terminal end portion, said first and second abutment surfaces are located substantially at said respective tab terminal end portion and said protruding rib terminal end, and each tab terminal end portion projects at least partially into an associated aperture (11).*

38. *The container as defined in claim 30 wherein said flexible tabs (9) and protruding rib (10) include respective tab terminal end portion and a protruding rib terminal end portion, said first and second abutment surfaces are located substantially at said respective tab terminal end portion and said protruding rib terminal end, each tab terminal end portion projects through an associated aperture, and each tab terminal end portion has a free edge defining said first abutment surface.*

39. *The container as defined in claim 30 wherein said flexible tabs (9) and protruding rib (10) include respective tab terminal end portion and a protruding rib terminal end* portion, said first and second abutment surfaces are located substantially at said respective tab terminal end portion and said protruding rib terminal end, each tab terminal end portion projects through an associated aperture, each tab terminal end portion has a free edge defining said first abutment surface, each tab terminal end portion projects generally axially upwardly toward said cover (5), and said second abutment surface is a lower surface of said protruding rib (10).

* * * * *